(12) United States Patent
Hoffmann (10) Patent No.: US 8,813,755 B2
(45) Date of Patent: Aug. 26, 2014

(54) SURGICAL COVER HAVING INTEGRATED FLUID BARRIER

(75) Inventor: Thomas Hoffmann, Heidenheim-Oggenhausen (DE)

(73) Assignee: Paul Hartmann AG, Heidenheim (DE)

(*) Notice: Subject to any disclaimer, the term of this patent is extended or adjusted under 35 U.S.C. 154(b) by 345 days.

(21) Appl. No.: 12/737,159

(22) PCT Filed: Jun. 12, 2009

(86) PCT No.: PCT/EP2009/004230
§ 371 (c)(1),
(2), (4) Date: Feb. 9, 2011

(87) PCT Pub. No.: WO2009/152993
PCT Pub. Date: Dec. 23, 2009

(65) Prior Publication Data
US 2011/0126845 A1    Jun. 2, 2011

(30) Foreign Application Priority Data
Jun. 18, 2008  (DE) .......................... 10 2008 029 051

(51) Int. Cl.
*A61B 19/00*    (2006.01)

(52) U.S. Cl.
USPC ........................................ 128/849; 604/357

(58) Field of Classification Search
USPC ........... 128/851–856, 849, DIG. 24; 604/357; 383/33, 63, 65
See application file for complete search history.

(56) References Cited

U.S. PATENT DOCUMENTS

| 5,222,507 | A | 6/1993 | Taylor |
| 5,901,706 | A | 5/1999 | Griesbach |
| 6,298,855 | B1* | 10/2001 | Baird ............................ 128/849 |
| 2007/0079834 | A1 | 4/2007 | Reyes |
| 2007/0135784 | A1* | 6/2007 | Tankersley ................... 604/357 |

FOREIGN PATENT DOCUMENTS

| EP | 1 842 563 | 10/2007 |
| WO | WO 2007/070097 | 6/2007 |

\* cited by examiner

*Primary Examiner* — Ophelia A Hawthorne
*Assistant Examiner* — Patricia Bianco
(74) *Attorney, Agent, or Firm* — Paul Vincent (57) ABSTRACT

A surgical cover has a second absorbent region which is overlapped by a fluid absorbent and fluid permeable material section having outer edges and adjoining edge regions. The surgical cover as such extends in a longitudinal direction LR between an upper end and a lower end. The absorbent material section is undetachably fixed across the entire circumference on the upper side of the base cover material of the surgical cover and is substantially not connected to the base cover material outside of the edge regions such that a pocket is formed between the absorbent material section and the fluid impermeable base cover material. At least one of the edge regions of the absorbent material section has a fluid barrier formed by a joining element which undetachably fixes the material section to the upper side of the base cover material.

30 Claims, 7 Drawing Sheets

SURGICAL COVER HAVING INTEGRATED FLUID BARRIER

This application is the national stage of PCT/EP2009/004230 filed on Jun. 12, 2009 and claims Paris Convention Priority to DE 10 2008 029 051.3 filed Jun. 18, 2008.

BACKGROUND OF THE INVENTION

The invention concerns a disposable surgical cover having absorbent areas. Surgical covers of this type have a liquid-impermeable base cover material with a lower side facing the patient during use, and an upper side, wherein the upper side has an absorbent layer, a first absorbent area and at least one second absorbent area. The second absorbent area is thereby covered by a liquid-absorbent and liquid-permeable material section having peripheral edges and adjoining edge areas. The surgical cover as such extends in a longitudinal direction LR between an upper end and a lower end.

Disposable surgical covers include covers for any type of operation, which are intended for single use only.

Surgical covers are used for covering the patient in a sterile fashion during a surgical intervention. The essential properties of a surgical cover include a barrier function in view of germ tightness and liquid penetration resistance, and also sufficient material strength (tear resistance and tensile strength), moreover minimum dispersion of particles to the surroundings (linting exposure) and additionally microbiological purity. All these requirements are described in EN 13795 part 1 2003, part 2 2005, part 3 2006.

In addition to the above-mentioned normatively defined requirements, in practice the surgical cover must also fulfil the requirement for sufficiently good liquid management during the surgical intervention. In practice, a surgical cover should be suitable for surgical interventions which involve little amounts of liquid up to very large amount of liquids, often even involving torrent liquid volumes.

There are conventional surgical covers which include measures for improving the collection of liquid that is accumulated during an operation and leaves the field of operation.

The liquid absorptive capacity of the base cover materials varies greatly. When absorption is regarded as being insufficient, some areas of the surgical covers may be provided with absorbent reinforcements.

For example U.S. Pat. No. 3,902,484 discloses a surgical cover of a base cover material with a material section which is disposed on the upper side and consists of a foil layer bordering this upper side, and of an absorbent layer of foamed material.

There are also conventional surgical covers with an absorbent upper side and a single-layer absorbent pad that is fixed thereto by means of hot melt adhesive, applied in the form of strips.

In practice, surgical covers are mostly used in an inclined position during use. Despite the absorptive capacity of an absorbent material section that is attached to the base cover material, and also despite its lateral distribution capacity, the absorbed liquid wanders downwards by gravity to the lower edge of the absorbent material section during relatively long surgical interventions, and continues, following the base cover material, to the lower edge of the base cover material. That is where it starts to drip out of the surgical cover and contaminate the areas located therebelow and, in particular, i.a. the floor of the operating room.

In order to counteract this problem, the surgical covers are additionally provided with a separately attached specially constructed liquid-collecting bag for operations involving very large amounts of liquid, often with torrent liquid volumes. The disadvantage of this attached bag is mainly the bulky construction that impedes the work of the surgeon.

There are also integrally attached liquid-collecting bags. WO 02/41800 A2 and EP 0 631 760 B1 disclose surgical covers which have a groove that is open towards the operating field and is formed by folding part of a material section and fixing onto itself by means of hook/loop mechanisms or other detachable fixing means. U.S. Pat. No. 4,089,331 and U.S. Pat. No. 3,791,382 also disclose a surgical cover with a reinforcing section that is disposed around the operating window and from which a collecting groove is provided by folding the material section several times.

U.S. Pat. No. 5,464,024 discloses a reusable surgical cover with a liquid-collecting groove that surrounds and is open towards the operating window. This collecting groove is obtained by folding a liquid-repellent material section, which is disposed around the operating window, in the direction towards the operating window and partially fixing this material section onto itself.

WO 2006/0389948 A1 describes a surgical cover consisting of a central cloth section with operating window and two further cloth sections which are attached to the respective longitudinal edges of the central cloth section. The ends of the central cloth section are then folded and fastened onto the cloth section, thereby forming a cuff for collecting liquid.

It is the underlying purpose of the invention to improve a surgical cover of the above-mentioned type in such a fashion that it provides sufficient absorbent capacity for liquids and sufficient retardation of liquid leakage at the same time ensuring simple and inexpensive construction of the surgical cover.

SUMMARY OF THE INVENTION

This object is achieved in accordance with the invention by a surgical cover comprising the features of the independent claim.

In order to solve this object, a disposable surgical cover of the above-mentioned type is proposed, in which the absorbent material section is undetachably fixed across the entire circumference in the edge areas to the upper side of the base cover material and wherein the absorbent material section is substantially not connected to the base cover material outside of the edge areas, such that a bag is formed between the absorbent material section and the liquid-impermeable base cover material. At least one of the edge areas of the absorbent material section has a liquid barrier, at least in sections, wherein the liquid barrier is formed by a joining means which undetachably fixes the material section to the upper side of the base cover material. This is based on the understanding that the second absorbent area is formed by the broad extension of the absorbent material section and also by the broad extension of the base cover material which is disposed therebelow and is also covered by the absorbent material section. The remaining surface of the upper side of the base cover material which is not covered by an absorbent material section forms a first absorbent area.

"Outside of the edge areas substantially not connected to the base cover material" means that the surface of the absorbent material section, which surface remains outside of the fixed edge areas, comprises additional bonds between the absorbent material section and the base cover material with an area ratio of maximally 10%, in particular maximally 5%, moreover, in particular, maximally 2.5% with respect to the overall surface of the absorbent material section.

"Across the entire circumference" thereby means the entire circumference which is described by the limiting line of a flat planar structure. The planar structure may thereby have a regular broad extension of a polygon, such as e.g. a square, a rectangle. The flat planar structure may also be described by a limiting line which, starting from an outer contour of the planar structure which is primarily perceived by the viewer, has an indentation that extends in a radially inward direction, as e.g. in the form of a slotted recess with an otherwise rectangular planar structure. The circumference is the sum of all limiting lines.

"Longitudinal direction" thereby means any broad extension between two opposing ends of the surgical cover. The upper and lower ends of the surgical cover are determined by the arrangement relative to the floor level during use of the surgical cover.

An upper and a lower end in the longitudinal direction of the surgical cover are determined by the intended purpose of use of the respective surgical cover.

The arrangement of the surgical cover in the longitudinal direction, which is preferred for the respective purpose of use, is displayed to the user, i.e. the medical staff, preferably by orientation guides.

The orientation guides may thereby have different designs, e.g. in the form of symbols, diagrams, arrows with indication of direction, or also as schematic representation of human body parts such as feet or head which suggest to the user where the upper and lower ends of the surgical cover are. Another advantageous orientation guide for detecting an upper and a lower end are fixing means provided by the manufacturer along the upper edge of the surgical cover, and thereby advantageously on the lower side of the base cover material for fixing the surgical cover to the patient or to other previously applied covers.

The invention has shown that this type of construction of a surgical cover has substantial advantages.

On the one hand, the combination of a liquid-absorbent and permeable material section with an absorbent upper side of the base cover material, which is disposed directly therebelow, without interposing a liquid-impermeable intermediate layer, also enables further transport of the liquid that is primarily absorbed by the absorbent material section to the base cover material, where it is absorbed and distributed. This provides an optimized liquid absorbent capacity in the critical areas of a surgical cover that are possibly exposed to large amounts of fluid. The absorptive capacity of materials is normally accomplished by the material composition and the specific selection and/or thickness thereof, and/or a high surface density. For this reason, separately designed, thick reinforcing materials are normally applied to a surgical cover. The combination of the absorbent layer of the base cover material, which already forms the actual surgical cover, with deliberately zonally arranged absorbent material sections provides areas having an optimized surface density, thereby saving material and therefore costs.

On the other hand, the substantially only border fixation of the absorbent material section to the base cover material between the two material layers produces a bag in which liquid is additionally collected and distributed in a type of glass plate effect, i.e. adhesive force between the material layers.

The border fixation moreover does not unnecessarily stiffen the surgical cover. For this reason, the drapeability of the surgical cover is also only very slightly impaired. It is also advantageous for the fixation of the absorbent material section to be substantially only on borders, since the absorptive capacity provided by the broad extension of the absorbent material section is thereby only minimally impaired.

It has also turned out that joining means, which simultaneously form liquid barriers in the edge areas, may be used for fixing the absorbent material section to the base cover material. The integral bag which is substantially only obtained by border fixation of the absorbent material section to the base cover material is sealed, at least in sections, along its limiting lines. This creates a collecting device which is integrated in the surgical cover, i.e. a liquid collecting reservoir, which advantageously does not need any further material layers.

This yields an overall surgical cover with optimized liquid management with minimum construction expense.

The joining means may be any means that are used for fixing materials, i.e. fixing the absorbent material section to the base cover material.

The joining means is preferentially selected from the group of hot melt adhesive, single-sided or double-sided adhesive tape, welding points, and thereby, in particular, ultrasonic welding points, thermal welding points and calender welding points.

The joining means are thereby designed in such a fashion that the undetachable fixation of the edge areas of the absorbent material section to the upper side of the base cover material forms a liquid barrier.

Owing to their material properties, the joining means themselves may have liquid barrier properties.

Hot melt adhesives are stable under wet conditions and have hydrophobic properties. Hot melt adhesives, in particular, in the form of continuous strips, form a liquid barrier. The hot melt adhesive may additionally partially penetrate deeply into the materials to be connected, close the pores and thereby increase their barrier effect.

An adhesive tape as such has a liquid-impermeable polymeric layer which is adjoined on one or both sides and/or only in some respective areas by an adhesive coating, which generates the actual undetachable connection between the absorbent material section and the base cover material.

Welding points may be generated by different methods, e.g. by ultrasound, thermally, or calendering. Welding methods thereby directly act on the material subjected to the welding method, which results in forming a joint on or at the correspondingly treated locations and additionally also in a change in material properties (e.g. transforming the fluffy character of a non-woven material into a foil-like character). The bonding strength of the respective welding points can be adjusted through selection of the ultrasonic strength, the temperature or the pressure.

In an advantageous further development of the invention, the surgical cover has at least one recess within the second absorbent area. The recess may thereby have a different design. This is based on the understanding that a recess may be an opening that is delimited by material across its entire circumference. The opening may thereby have any contour, i.e. be round, oval, square, rectangular or polygonal with rounded corners.

The recesses may have any dimension. The circular openings advantageously have a dimension of 4 to 12 cm, oval openings have a size of 10×14 cm, in particular 5×7 cm. Openings of any contour may also have a size of 20×30 cm.

A recess may also be formed as an indentation in the direction towards the center of the surgical cover starting from the outer contour of the planar structure that is primarily perceived by the viewer. The indentation may thereby have any contour, e.g. the form of a slotted or U-shaped indentation, thereby forming two material tabs that delimit this recess. Indentations of this type may have any dimension.

U-shaped indentations of this type may preferably have a dimension of a width of 5 to 10 cm and a length of 40 to 100 cm.

Surgical covers comprising a recess may be advantageous for specific operations. A surgical cover having a recess thereby covers the area of the patient, in which the surgical intervention is planned, in an optimized fashion, such as e.g. as a direct delimitation of the operating field. The recess of the surgical cover can e.g. also receive extremities of the patient such as an arm or a leg or other exposed areas such as shoulder, knee, and thereby surround them.

The second absorbent area preferentially surrounds the recess, wherein the absorbent material section has inner peripheral edges and inner edge areas and also outer peripheral edges and outer edge areas which are associated with the edges of the recess.

The second absorbent area preferentially directly surrounds and borders the recess.

In a further advantageous embodiment, the second absorbent area surrounds the recess at a radial separation. A radially separated arrangement of the absorbent material section with respect to the edges of the recess is provided, in particular, when the actual recess is primarily surrounded by a rubber-elastic material in the form of a cuff. For surgical covers, the recesses of which are provided for receiving extremities, a rubber-elastic cuff is advantageous for a better fit.

The second absorbent area may thereby surround the recess at least in sections or, in particular, across the overall circumference.

"Inner peripheral edges" or "inner edge areas" are thereby defined with respect to the recess as the proximal ones, i.e. the peripheral edges or edge areas of the absorbent material section surrounding the recess, which directly border the edges of the recess.

"Outer peripheral edges" or "outer edge areas" are thereby defined with respect to the recess as the distal ones, i.e. the peripheral edges or edge areas of the absorbent material section that surrounds the recess, which are remote from the edges of the recess.

In a particularly advantageous fashion, the inner peripheral edges of the absorbent material section are substantially flush with the edges of the recess. With this largely edge-flush arrangement of the absorbent material section, the liquid coming out of the operation field can be directly primarily bound by the optimized area.

"Arranged substantially flush with the edges" means that a minimum production-related tolerance of the arrangement of the inner peripheral edges of the absorbent material section with respect to the edges of the recess is still supported by the inventive idea, i.e. either the inner peripheral edges extend past the edges of the recess or the inner peripheral edges terminate within a radial separation from the edges of the recess.

"Production-related tolerances" means a deviation of up to maximally +/−5 mm.

In a further design of the surgical cover, the absorbent material section is disposed closer to the upper end of the surgical cover than to the lower end of the surgical cover.

On the basis that the upper end describes the end that is closest to the operating field during use of the surgical cover, this arrangement offers optimized liquid binding capacity and also liquid retardation. In particular, when a large amount of liquid is present, the danger of contamination due to rapid dripping can be reduced. In correspondence with the upper end and the lower end of the surgical cover, the absorbent material section also has an "upper peripheral edge" and an "upper edge area" and a "lower peripheral edge" and a "lower edge area". The lower peripheral edge and the lower edge area are each laterally adjoined by the further peripheral edges and the further edge areas. The sum of all peripheral edges then forms the circumference of the absorbent material section.

This embodiment of the surgical cover is particularly advantageous when the upper peripheral edge of the absorbent material section is arranged to be substantially flush with the upper end of the surgical cover.

"Substantially flush with the upper end of the surgical cover" means that a minimum production-related tolerance of the arrangement of the upper peripheral edge of the absorbent material section with respect to the upper end is still supported by the inventive idea, for example that the peripheral edge of the absorbent material section extends past the upper end of the surgical cover or that the peripheral edge of the absorbent material section extends to just below the upper end.

In a particularly advantageous embodiment, the absorbent material section has a liquid barrier on a lower edge area. In this fashion, the liquid that moves downwards towards the floor by gravity can be held back.

In the further development of a surgical cover, the edge areas of the material section, which each laterally adjoin a lower edge area of the material section, also have a liquid barrier.

The lateral continuation of the liquid barrier advantageously forms a bag with a leakage protection that is surrounded by three edges.

In a further preferred embodiment, only the outer edge areas of the material section have a liquid barrier.

In a further preferred embodiment, all edge areas of the absorbent material section have a liquid barrier.

With particular preference, different joining means are used such that a first liquid barrier and at least one further liquid barrier, which is different from the first liquid barrier, are formed in the edge areas.

Surgical covers are mostly arranged by trained medical staff in a standardized fashion for a defined field of use, such that e.g. there is a defined arrangement with respect to the operating field.

Due to the arrangement during the intended use of the surgical cover, the problems due to liquid migration following gravity, may be different in different areas. It may accordingly be advantageous to use different joining means and thereby provide different types of liquid barriers.

The liquid barrier provided by the joining means may thereby be disposed on the inner side and/or the outer side of the absorbent material section. The arrangement of the liquid barrier results from the arrangement and fixation of the respective joining means.

There are different feasible arrangements of the joining means for forming liquid barriers in the edge areas.

In a first preferred embodiment, the joining means is flatly disposed between the upper side of the base cover material and the inner side of the absorbent material section.

In a second preferred embodiment, the joining means is flatly disposed between the upper side of the base cover material and the inner side of the absorbent material section, wherein the liquid barrier formed by the joining means extends across the width of the fixed edge area towards the bag. This means that the joining means is disposed, in particular, between the upper side of the base cover material and the inner side of the absorbent material section, thereby directly connecting them, and extends further towards the bag, wherein the joining means is then only disposed on the inner side of the absorbent material section.

In a third preferred embodiment, the joining means is disposed between the upper side of the base cover material and the inner side of the absorbent material section thereby directly connecting them, and extends further past the peripheral edge of the absorbent material section and is then folded back and fixed to the upper side of the absorbent material section. This preferred embodiment of the joining means is particularly advantageous, since the absorbent material section is additionally also sealed on the peripheral edge and the peripheral edge is sealed from the outside by the liquid barrier generated by means of the joining means.

In a fourth preferred embodiment, the joining means is disposed on the upper side of the base cover material and extends further past the peripheral edge of the absorbent material section and is then folded back and fixed to the upper side of the absorbent material section. This preferred embodiment of the joining means is also advantageous, since the absorbent material section is additionally also sealed on the peripheral edge and the peripheral edge is sealed from the outside by the liquid barrier generated by the joining means.

In a fifth preferred embodiment, the joining means is configured in the form of a groove and the two legs of the groove are each fixed, starting from the distal folding edge, to the upper side of the base cover material and to the inner side of the absorbent material section such that the groove opens towards the bag. The folding edge may thereby advantageously be disposed in the center. The folding edge may also be eccentrically disposed with respect to the overall width of the joining means.

In a sixth preferred embodiment, the joining means covers both an edge area on the outer side of the absorbent material section and also a directly bordering part of the upper side of the base cover material.

In a seventh preferred embodiment, the joining means is designed in the form of welding points. The welding points may thereby advantageously be ultrasonic welding points, thermal welding points (thermobonding) or calender welding points. The welding points are thereby advantageously arranged in the form of a welding pattern. The welding pattern may thereby result from the arrangement of the welding points and their separation from each other, i.e. the welding point density. The welding pattern may also result from the varying depth of the welding points.

The joining means in the form of a welding pattern extends at least across the edge area. The joining means advantageously also extends past the peripheral edge and the bordering part of the base cover material.

With particular preference, the welding pattern is designed in such a fashion that it has a decreasing profile with respect to bonding point depth and/or bonding point density and/or bonding point strength in the direction from the peripheral edge towards the bag. The bonding strength of the respective welding points can be adjusted through selection of the ultrasonic strength or the temperature or the pressure.

The welding pattern preferentially comprises a first subregion which is disposed proximally with respect to the peripheral edge and has a first welding part pattern, and a further second subregion, facing the bag, with a second welding part pattern. The first and the second welding part patterns are, in particular, advantageously formed by a welding device with a temperature profile.

The first welding part pattern comprises, in particular, welding points for undetachably fixing the absorbent material section to the base cover material, and the second welding part pattern has only welding points which are only disposed on the absorbent material section.

The invention has also turned out to be particularly advantageous when the liquid barrier extends past the width of the fixed edge area towards the bag.

It is additionally particularly advantageous for the undetachably fixed edge areas to cover a surface of 2 to 45%, in particular of 2 to 35%, moreover, in particular, of 2 to 30% with respect to the overall surface of the absorbent material section.

It is moreover also advantageous for the fixed edge areas to have a width B of 0.5 to 10 cm, advantageously of 1 to 8 cm, moreover advantageously of 1.5 to 6 cm.

The width in the fixed edge areas preferentially varies. The lower edge area preferentially has a larger width B compared to the further edge areas that laterally adjoin the lower edge and/or compared to the upper edge area.

During normal use of a surgical cover, the liquid that is discharged and comes out of the operating field during a surgical intervention should be optimally bound.

The second absorbent area herewith provides an area within the surgical cover that is optimized for this critical moment. It is thereby particularly advantageous for the absorbent material section that covers the second absorbent area to have a larger absorptive capacity AK than the material forming the first absorbent area. It has also turned out to be advantageous for the absorbent material section to have an absorptive capacity AK which is larger by at least 25%, in particular at least 50%, in particular at least 100%, in particular at least 150%, moreover, in particular at least 200%, moreover, in particular 250%, moreover, in particular at least 300% than the material forming the first area.

The respective material is measured according to the method ISO/DIS 9073-6: 2001 to obtain the absorptive capacity AK (expressed in $g/m^2$). The absorptive capacity measured according to this method (expressed in g/g, i.e. liquid weight relative to the weight of the material) is then referred to the surface density of the material, thereby obtaining the unit $g/m^2$.

The material forming the absorbent material section advantageously has an absorptive capacity AK of at least 150 $g/m^2$, in particular, at least 200 $g/m^2$, in particular at least 250 $g/m^2$, in particular at least 300 $g/m^2$, in particular at least 350 $g/m^2$, with the absorptive capacity AK being measured and calculated according to the above-described method.

The material forming the first area preferentially has an absorptive capacity AK of 50 to 250 $g/m^2$, in particular 80 to 220 $g/m^2$, moreover, in particular 100 to 200 $g/m^2$, with the absorptive capacity AK being measured and calculated according to the above-described method.

It has also turned out to be advantageous for the second absorbent area to have a broad extension of 2 to 65%, advantageously 2 to 55%, moreover advantageously 2 to 45% with respect to the overall surface of the base cover material. With this surface ratio of the second absorbent area, the surgical cover still provides an overall optimized liquid management and at the same time reduces material and therefore costs.

The surface density of the absorbent material section is advantageously 25 to 100 $g/m^2$, in particular 35 to 80 $g/m^2$, moreover, in particular 45 to 65 $g/m^2$, moreover advantageously 50 to 60 $g/m^2$.

In a particularly advantageous fashion, the absorbent material section is formed by a single-layer or multi-layer non-woven material. The absorbent material section is preferentially formed by a hydrophilized non-woven material with one or several layers of spunbond (S) and/or meltblown (M). The absorbent material section is preferentially formed by a hydrophilized SMS non-woven polypropylene material.

In a particularly advantageous fashion, the base cover material is formed from a single-layer or multi-layer non-woven material, in particular, a laminate of one or more spunbonded and/or meltblown non-woven layers or a non-woven foil composite.

The base cover material is preferentially formed by a non-woven foil composite with the foil facing the lower side.

In case of a non-woven foil composite, the surface density of the non-woven material is advantageously 10 to 40 g/m$^2$, in particular 10 to 35 g/m$^2$, moreover, in particular 15 to 35 g/m$^2$, moreover, in particular 20 to 35 g/m$^2$. The foil has a surface density of advantageously 15 to 35 g/m$^2$, in particular 20 to 30 g/m$^2$.

The base cover material is preferentially formed by a non-woven foil composite with a hydrophilized non-woven material with one or more spunbond and/or meltblown layers.

The foil in the non-woven foil composite is advantageously not a microporous foil.

The non-woven foil composite may be laminated in any fashion, the non-woven foils are advantageously connected through thermobonding and/or hotmelt. With particular preference, the base cover material is formed by a composite of hydrophilized spunbonded non-woven material of polypropylene with a PE foil.

In another advantageous further development of the surgical cover, the upper side has further second absorbent areas.

The second and the further second absorbent area may be arranged on the upper side such that they directly border each other or are arranged at a distance from each other. The second absorbent areas may advantageously differ with respect to their respective broad extension.

The second absorbent areas are moreover advantageously covered by absorbent material sections which differ from each other, e.g. with respect to absorptive capacity, surface density, material composition.

The second absorbent area and also the further second absorbent area advantageously have a recess.

Particularly advantageous embodiments of the inventive surgical covers:

One particularly preferred embodiment of the surgical cover comprises a base cover material consisting of a non-woven foil composite, wherein the non-woven layer facing the upper side consists of a hydrophilized spunbonded non-woven material, in particular, of a hydrophilized PP spunbonded non-woven material. The surface density of the spunbonded non-woven layer is 20 to 35 g/m$^2$. The absorptive capacity of this non-woven material according to the above-described method is 120 to 180 g/m$^2$.

The absorbent material section covering the second absorbent area is formed from a hydrophilized SMS non-woven material, in particular, of a hydrophilized PP-SMS non-woven material with a surface density of 50 to 60 g/m$^2$. The absorptive capacity of this SMS non-woven material according to the above-described method is 220 to 330 g/m$^2$. The surgical cover extends in the longitudinal direction LR between an upper end and a lower end, wherein the absorbent material section is disposed closer the upper end of the surgical cover than to the lower end of the surgical cover. The material section of this arrangement also correspondingly has an upper, a lower and adjoining lateral peripheral edges, and corresponding edge areas that border these peripheral edges. The upper peripheral edge of the material section is preferentially substantially flush with the upper end of the surgical cover.

The upper edge area, the lower edge area and the adjoining lateral edge areas have a liquid barrier. This liquid barrier is formed by joining means which undetachably fix the material section to the upper side of the base cover material.

Towards this end, a joining means is used for the lower edge area, which differs from that of the other edge areas (i.e. the edge areas laterally adjoining the lower edge, and the upper edge area) such that the lower edge area has a first liquid barrier and the further edge areas have a further liquid barrier, i.e. one that differs from the first liquid barrier.

The above-described surgical cover advantageously utilizes the following joining means combinations.

In a first preferred variant, the joining means is configured to be groove-shaped in the lower edge area in correspondence with the above-described fifth embodiment of the joining means.

In a second preferred variant, the joining means is designed and fixed in the lower edge area in correspondence with the fourth embodiment of the joining means explained in more detail above.

In a third preferred variant, the joining means is designed and fixed in the lower edge area in correspondence with the sixth embodiment of the joining means explained in more detail above.

In a fourth preferred variant, the joining means is designed and fixed in the lower edge area in correspondence with the seventh embodiment of the joining means explained in more detail above.

In a fifth preferred variant, the joining means is designed and fixed in the lower edge area in correspondence with the second embodiment of the joining means explained in more detail above.

In a sixth preferred variant, the joining means is designed and fixed in the lower edge area in correspondence with the third embodiment of the joining means explained in more detail above.

All above-mentioned variants advantageously use joining means in the further edge areas, which, in correspondence with the first embodiment which is explained in more detail or also advantageously in correspondence with the second preferred embodiment of the joining means which is explained in more detail, are flatly arranged between the upper side of the base cover material and the inner side of the absorbent material section. These edge areas are, in particular, fixed by means of a hot melt adhesive. These edge areas are moreover, in particular, fixed by a double-sided adhesive tape that is stable under wet conditions.

In a further advantageous design of the surgical cover, the lower edge area and also each laterally bordering edge area have a liquid barrier. The above-described variants of joining means are advantageously also continued in the lower edge area in the laterally bordering edge areas such that only the upper edge area is advantageously fixed with a flat joining means disposed between the upper side of the base cover material and the inner side of the absorbent material section, i.e. in particular, in the form of a hot melt adhesive or also a double-sided adhesive tape, thereby forming the further liquid barrier.

In a further advantageous design of the surgical cover, all edge areas, i.e. the upper and the lower and also the edge areas laterally adjoining the lower edge area, have a liquid barrier. The liquid barrier is advantageously formed by the same joining means.

In a further particularly preferred embodiment, the above-described surgical cover has a recess. The joining means used in the respective outer and inner edge areas differ such that a first liquid barrier and a further liquid barrier that is different from the first liquid barrier are correspondingly formed, at least in sections, in the outer and inner edge areas.

In one particularly preferred further development, different joining means are provided in the outer and inner edge areas and also in the upper and lower edge areas thereof and in the edge areas laterally adjoining the lower edge area.

Further features, advantages and details of the invention can be extracted from the attached claims, the drawing and the following description of preferred embodiments of the invention. Patent protection is claimed for the above-mentioned features and the features mentioned below in the claims irrespective of any dependence and in arbitrary combination with each other.

BRIEF DESCRIPTION OF THE DRAWING

The invention is explained in more detail below with reference to the drawings.

DESCRIPTION OF THE PREFERRED EMBODIMENT

Figure 1:
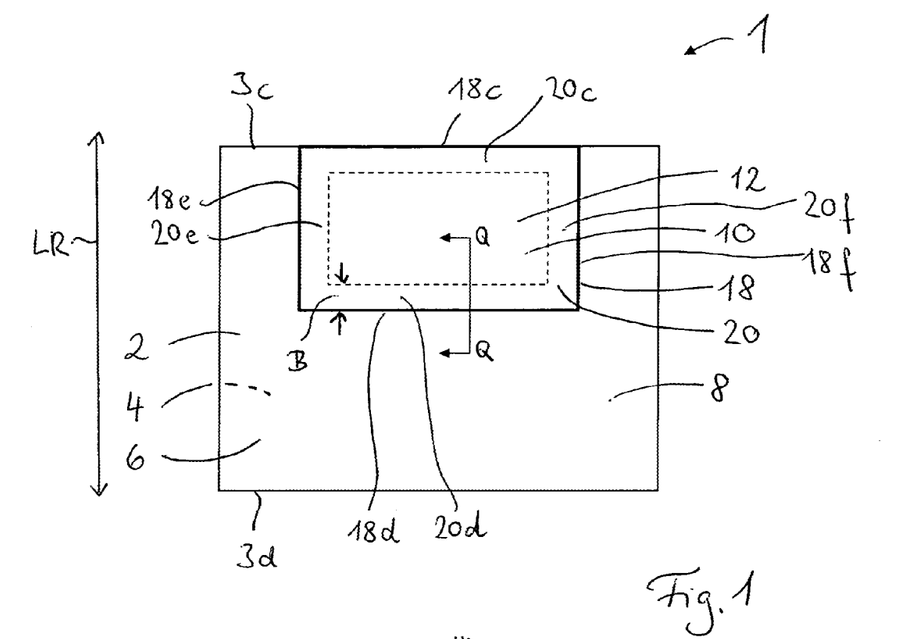
FIG. 1 shows a schematic top view of an inventive surgical cover.

FIG. 1 schematically shows a top view of a surgical cover 1 of a preferred rectangular embodiment. The surgical cover 1 thereby has an upper end 3c and a lower end 3d in a longitudinal direction LR. The longitudinal direction LR is thereby defined as any broad extension between two opposing ends of the flat structure. The upper end 3c and the lower end 3d of the surgical cover 1 are defined by the arrangement with respect to the floor level during use of the surgical cover.

The surgical cover 1 thereby has a base cover material 2 which is impermeable to liquid. The base cover material 2 has a lower side 4 facing the patient during use, and an upper side 6. This upper side 6 has an absorbent layer. The upper side 6 additionally has a first absorbent area 8 and a second absorbent area 10.

This second absorbent area 10 is thereby covered by a material section 12. The absorbent material section 12 has peripheral edges 18 and edge areas 20 bordering the peripheral edges 18. In correspondence with the upper end 3c and the lower end 3c of the surgical cover 1, the absorbent material section 12 also has an upper peripheral edge 18c and an upper edge area 20c and a lower peripheral edge 18d and a lower edge area 20d. The lower peripheral edge 18d and the lower edge area 20d are each laterally adjoined by further peripheral edges 18e, 18d and further edge areas 20e, 20f.

The sum of all peripheral edges 18c, 18d, 18e, 18f then forms the circumference of the absorbent material section 12.

The second absorbent area 10 is then defined by the broad extension of the absorbent material section 12. The second absorbent area 10 contains the absorbent material section 12 and also the base cover material 2 that is projected in the Z-direction (as indicated in FIG. 2) which is disposed therebelow and is defined by the same broad extension.

The remaining surface of the upper side 6 of the base cover material 2, which is not covered by an absorbent material section 12, forms the first absorbent area 6. The edge areas 20 have a width B of 1.5 to 6 cm.

Figure 2:
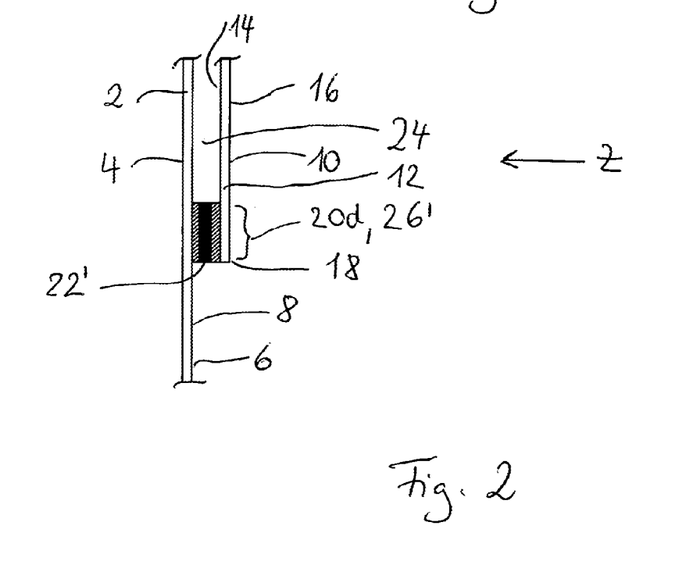
FIG. 2 shows a schematic side view of the surgical cover of FIG. 1 along the line Q-Q.

FIG. 2 shows a side view of the surgical cover 1 along the line Q-Q of FIG. 1. The section is only selected by way of example from the lower edge area of the absorbent material section. The arrangement as described below may be provided in all edge areas.

The edge areas 20c, 20d, 20e, 20f of the absorbent material section 12 are undetachably fixed across the entire circumference to the upper side 6 of the base cover material 2. The absorbent material section 12 is furthermore substantially not connected to the base cover material 2 outside of these edge areas 20c, 20d, 20e, 20f, wherein this means that there are further bonds between the absorbent material section and the base cover material outside of the already fixed edge areas in a ratio of maximally 10% related to the overall surface of the absorbent material section.

Fixation is thereby realized in such a fashion that a bag 24 is formed between the absorbent material section 12 and the liquid impermeable base cover material 2, the bag being closed across the entire circumference.

The edge areas 20c, 20d, 20e, 20f of the absorbent material section 12 have a liquid barrier 26' at least in sections, wherein this liquid barrier 26' is formed through undetachable fixation of the edge areas 20c, 20d, 20e, 20f of the absorbent material section to the upper side 6 of the base cover material 2 by the joining means 22'.

Figure 5:
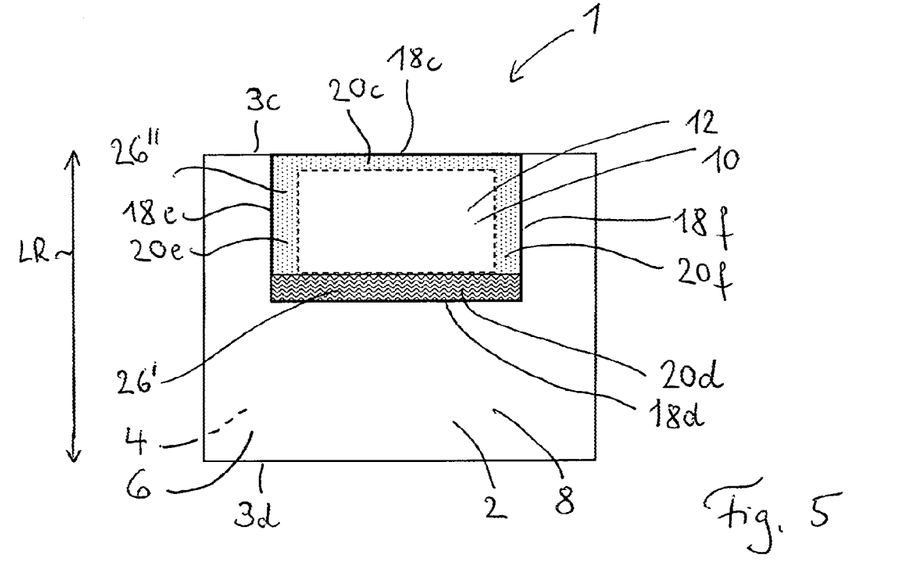
FIG. 5 shows a schematic top view of a surgical cover according to FIG. 1, with the liquid barriers being arranged in a preferred embodiment.

The liquid barrier 26' is formed at least in the lower edge area 20d, as is schematically illustrated in FIG. 5.

Figure 6:
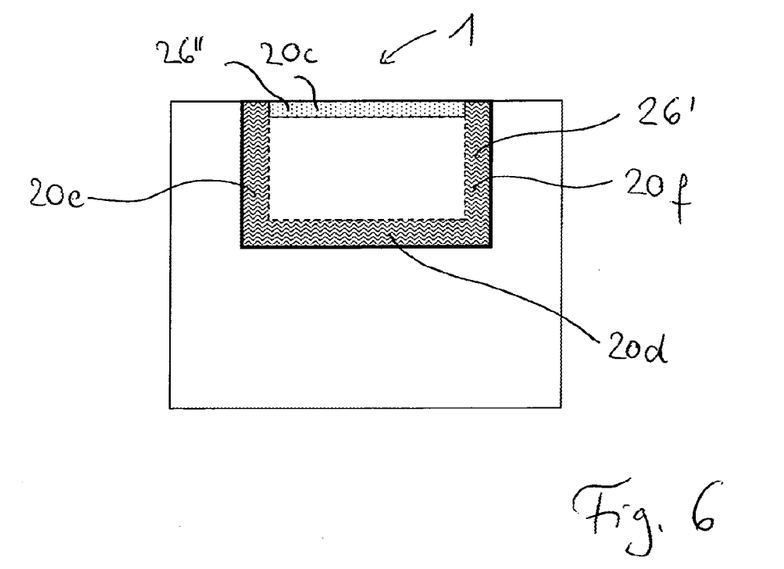
FIG. 6 shows a schematic top view of a surgical cover according to FIG. 1, with the liquid barriers being arranged in a further preferred embodiment.

The liquid barrier 26' may also be additionally formed in the edge areas 20e and 20f that laterally adjoin the lower edge area 20d, as is schematically illustrated in FIG. 6.

The joining means 22' may thereby be designed in accordance with different preferred embodiments as is described in more detail below in connection with FIGS. 8 to 18.

The absorbent material section 12 is thereby closer to the upper end 3c of the surgical cover 1 than to the lower end 3d of the surgical cover 1. The absorbent material section 12 is thereby even arranged in such a fashion that the upper peripheral edge 18c substantially terminates flush with the upper end 3c of the surgical cover 1.

Substantially flush with the upper end of the surgical cover means that minimum production-related tolerances of the arrangement of the upper peripheral edge 18c of the absorbent material section 12 with respect to the upper end 3c are still supported by the inventive idea, for example that the peripheral edge of the absorbent material section extends past the upper end 3c of the surgical cover or the peripheral edge 18c of the absorbent material section extends to just below the upper end 3c.

Figure 3:
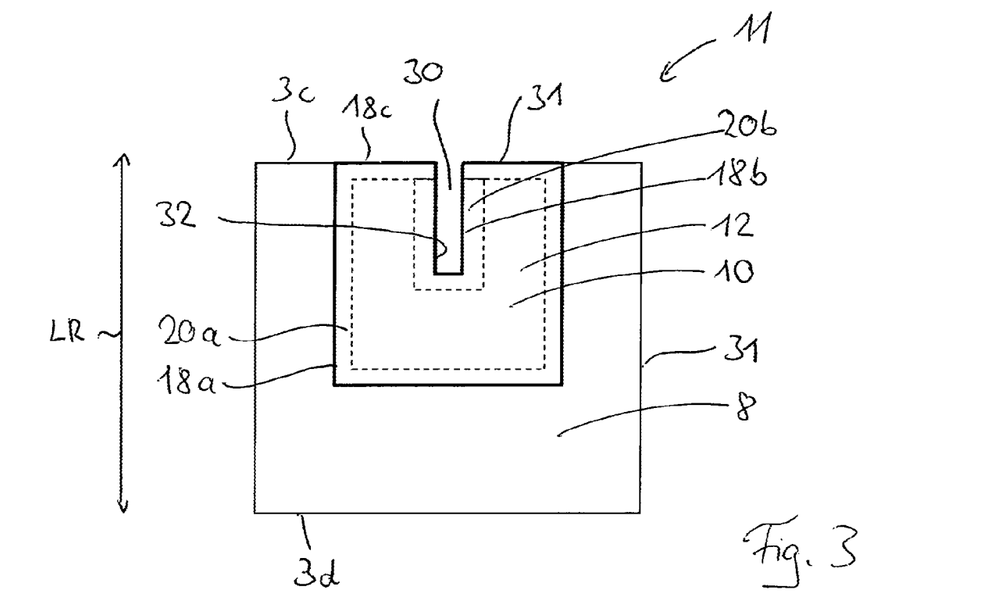
FIG. 3 shows a schematic top view of a further inventive surgical cover with a recess.
Figure 4:
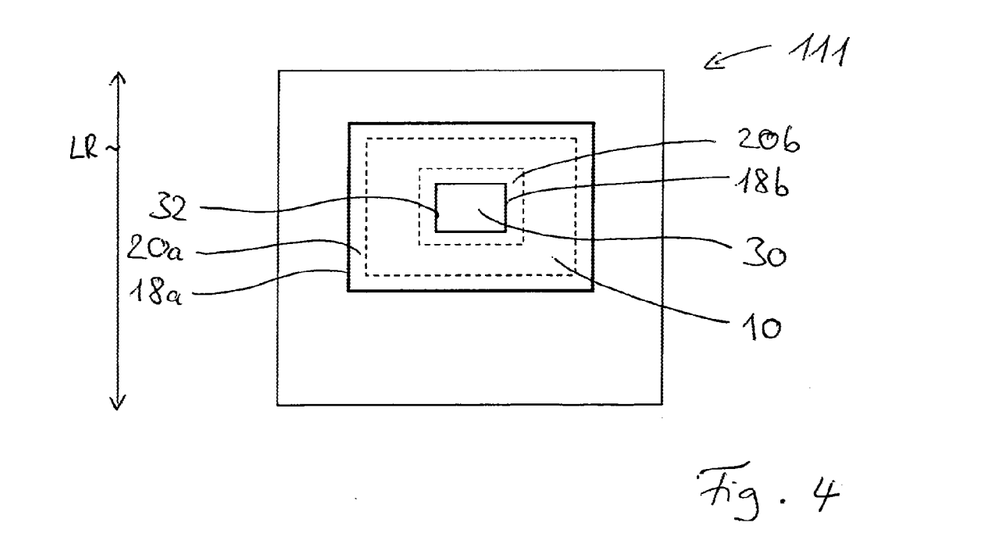
FIG. 4 shows a schematic top view of a further inventive surgical cover with a recess.

FIGS. 3 and 4 each show a schematic top view of further preferred embodiments of the surgical cover.

FIG. 3 shows a surgical cover 11 with a recess 30. An indentation is thereby guided, starting from a primarily perceived outer contour which is formed by the entirety of all outer edges 31, towards the center of the surgical cover, which then represents the recess 30. The recess 30 is defined by its edges 32, in the present case only incompletely.

Analogous to the above-described surgical cover 1, in this embodiment of the surgical cover 11, an absorbent and liquid-permeable material section 12 is also undetachably fixed in its edge areas across the entire circumference to the absorbent upper side of the liquid impermeable base cover material, thereby forming a bag.

The second absorbent area 10 directly surrounds the recess 30. The absorbent material section has inner peripheral edges 18b and inner edge areas 20b with respect to the edges 32 of the recess 30, and outer peripheral edges 18a and outer edge areas 20a. The circumference of the absorbent material section 12 is therefore formed by the sum of the inner and outer peripheral edges 18b, 18a. The inner peripheral edges 18b of the absorbent material section 12 are arranged substantially flush with the edges 32 of the recess 30. Arranged substantially flush with the edges means that a minimum production-related deviation of the arrangement of the inner peripheral edges 18b of the absorbent material section 12 with respect to the edges 32 of the recess 30 still supported by the inventive idea, for example that the inner peripheral edges extend past the edges of the recess or the inner peripheral edges terminate within a radial separation from the edges of the recess.

The absorbent material section 12 is thereby arranged closer to the upper end 3c of the surgical cover 11 than to the lower end 3d of the surgical cover 11. The absorbent material 12 is thereby even arranged in such a fashion that the upper peripheral edge 18c, which also represents an outer peripheral edge 18a, is disposed substantially flush with the upper end 3c of the surgical cover 11, wherein minimum production-related deviations from the edge-flush arrangement are still regarded as being in accordance with the invention.

FIG. 4 shows a surgical cover 111 with a recess 30 which is surrounded across the entire circumference by the second absorbent area 10. The absorbent material section 12 has inner peripheral edges 18b and inner edge areas 20b and also outer peripheral edges 18a and outer edge areas 20a with respect to the edges 32 of the recess. The inner peripheral edges 18b of the absorbent material section 12 are substantially flush with the edges 32 of the recess 30, wherein minimum production-related tolerances from the edge-flush arrangement are still regarded as being in accordance with the invention.

The absorbent material section 12 is thereby also fixed in its edge areas across the entire circumference to the upper side of the base cover material. At least one of the edges has a liquid barrier, at least in sections, which is formed by joining means during undetachable fixation of absorbent material to the upper side of the base cover material.

The joining means may thereby be designed in accordance with different preferred embodiments as is described in more detail below in connection with FIGS. 8 to 18.

FIGS. 5 and 6 show schematic top views of a surgical cover 1, as described in FIG. 1, of the preferred design, in which a lower edge area 20d of the absorbent material section 12 has a liquid barrier 26'. The liquid barrier 26' is formed by undetachably fixing a joining means to the upper side 6 of the base cover material 2. The joining means may thereby be designed in accordance with different preferred embodiments as is described in more detail below in connection with FIGS. 8 to 17.

The remaining edge areas 20c, 20e, 20f of the absorbent material section 12 are, however, also fixed to the upper side 6 of the base cover material 2, but these edge areas 20c, 20e, 20f have no liquid barriers, or in a further preferred embodiment, further liquid barriers 26" (see below) are formed by the joining means.

FIG. 6 schematically sketches a liquid barrier 26' which is additionally also formed in the edge areas 20e and 20f that laterally adjoin the lower edge area 20d. The upper edge area 20c of the absorbent material section 12 is indeed also fixed to the upper side 6 of the base cover material 2 but this edge area 20c does not have a liquid barrier, or in a further preferred embodiment, further liquid barriers 26" (see below) are formed by the joining means.

FIGS. 5 and 6 also outline that the liquid barriers 26', 26" may differ in that different joining means are used in the edge areas 20c, 20d, 20e, 20f of the absorbent material section 12.

FIG. 5 shows e.g. a surgical cover 1 with an absorbent material section 12, the lower edge area 20d of which has a first liquid barrier 26' which differs from the other liquid barrier 26" in the subsequent edge areas 20e, 20f and the opposing upper edge area 20c. The differences between the liquid barriers 26', 26" can be achieved through selection of the joining means. The lower edge area 20d has a first liquid barrier 26' which has better barrier properties than the further liquid barrier 26" in the other edge areas 20d, 20e, 20f.

FIG. 6 shows e.g. a surgical cover 1 with an absorbent material section 12, the upper edge area 20c of which has a further liquid barrier 26" compared to the other edge areas 20d, 20e, 20f. The surgical cover therefore has an integral bag with optimized leakage protection along three edge areas 20d, 20e, 20f.

The liquid barrier 26', 26" may also be formed in all edge areas 20c, 20d, 20e, 20f of the absorbent material section 12. The same joining means may be used in all edge areas 20c, 20d, 20e, 20f for fixing the absorbent material section to the upper side of the base cover material (not shown in the figure).

Figure 7:
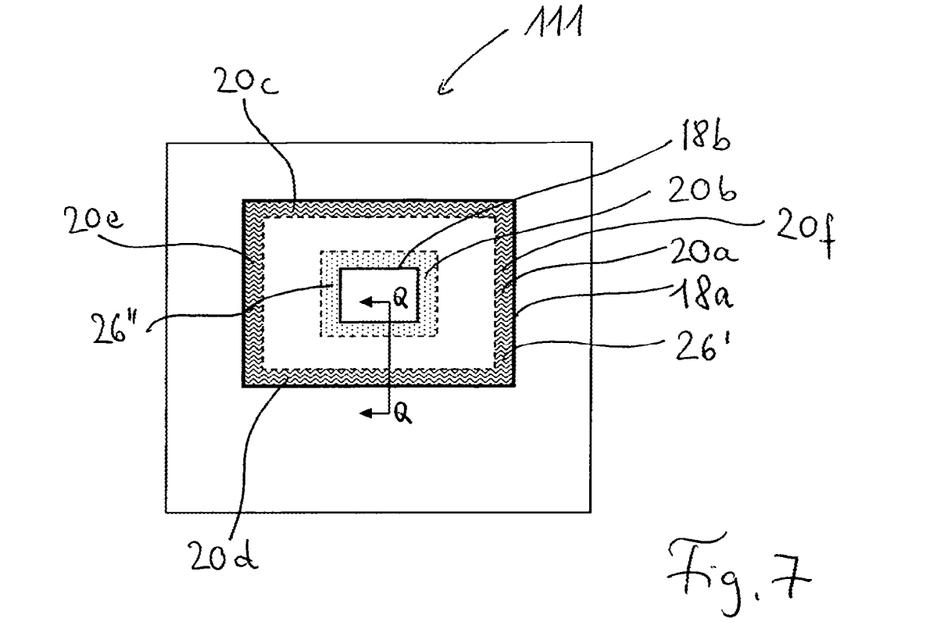
FIG. 7 shows a schematic top view of a surgical cover according to FIG. 3 with the liquid barriers being arranged in a preferred embodiment.
Figure 18:
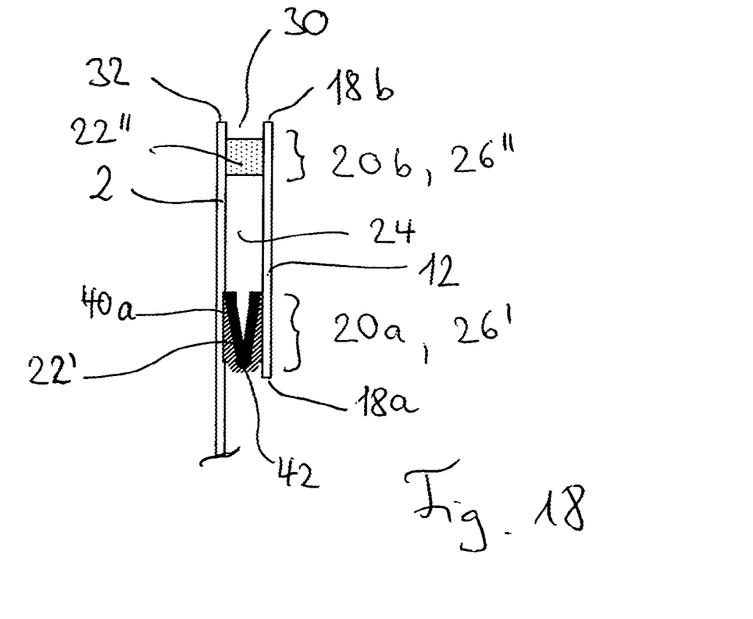
FIG. 18 shows a schematic view of the joining means, arranged in the surgical cover of FIG. 7, along the line Q-Q.

FIG. 7 schematically shows a top view of a surgical cover 111 with a recess 30, comprising the features as described above with reference to FIG. 4. The outer edge areas 20a, which are formed per se by the edge areas 20c, 20d, 20e, 20f, and the inner edge areas 20b can form liquid barriers 26', 26" by using different joining means. In particular, the design may be such that the outer edge areas 20a have different liquid barriers than the inner edge areas 20b. The first liquid barrier 26' may, in particular, advantageously have stronger barrier properties than a further liquid barrier 26". The surgical cover 111 in a side view along the line Q-Q is schematically illustrated in FIG. 18.

FIGS. 8 to 18 each schematically show the design of the joining means 22' according to a preferred embodiment.

Figure 8:
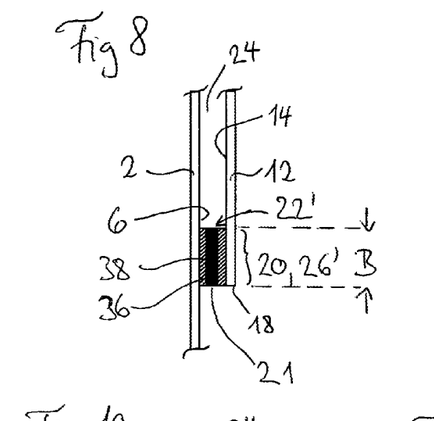
FIGS. 8 to 13 each show a schematic view of the joining means in a preferred embodiment, arranged in the surgical cover of FIG. 1 along the line Q-Q.

FIG. 8 shows a first preferred embodiment of the joining means 22'. The joining means 22' is flatly disposed between the upper side 6 of the base cover material 2 and the inner side 14 of the absorbent material section 12. The joining means 22' is thereby disposed such that its edge 21 facing towards the peripheral edge 18 of the absorbent material section 12 is substantially flush with the peripheral edge 18 of the absorbent material section. The joining means 22' also extends, starting from the peripheral edge 18, across the bordering edge area 20. The joining means 22' is thereby undetachably fixed in the edge area 20. With this undetachable fixation of the absorbent material section 12, the joining means 22' forms a liquid barrier 26' in this edge area 20. A bag 24 is formed between the absorbent material section 12 and the base cover material 2. The edge area 20 thereby has a width of 1.5 to 6 cm.

As is illustrated in FIG. 8, the joining means 22' of this type may comprise a polymeric layer 36, to the upper sides of which an adhesive coating 38 is applied on both sides. A double-sided adhesive tape may be used as a joining means of this type, the two adhesive surfaces of which provide the undetachable connection between the base cover material 2 and the material section 12 and thereby provide the overall liquid barrier 26'.

The joining means which is flatly arranged in this preferred embodiment may also be designed in the form of a hot melt strip (not shown in the figure).

Figure 9:
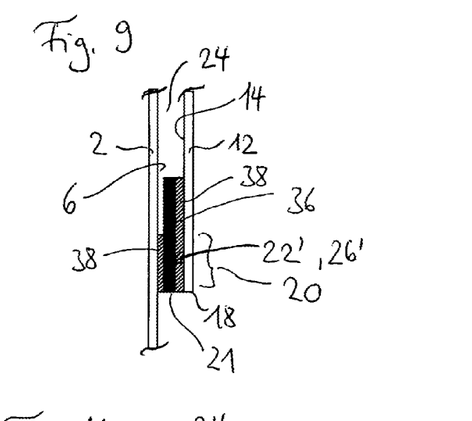

FIG. 9 shows a second preferred embodiment of the joining means 22'. Analogous to the arrangement of the joining means 22' according to FIG. 8, the joining means 22' is flatly arranged between the upper side 6 of the base cover material 2 and the inner side 14 of the absorbent material section 12. With this undetachable fixation of the absorbent material section 12, the joining means 22' forms a liquid barrier 26' in this edge area 20.

This embodiment is advantageous in that the liquid barrier 26' extends in the direction towards the bag 24 past the width of the edge area 20 that is directly fixed to the upper side 6 of the base cover material 2.

The joining means 22' therefore has an adhesive coating 38 of varying extension on the two upper sides of the polymeric layer 36. For a joining means of this type, a double-sided adhesive tape may be used, one upper side of which is provided with an adhesive coating across its overall surface and the opposite upper side of which has an adhesive coating only in some areas. Advantageously at most half, moreover advantageously at most only one quarter of the width of the adhesive tape is designed to be adhesive. The correspondingly other part is thereby not adhesive which is achieved in that no adhesive coating is applied or that the adhesive coating that extends over the entire width of the tape is subsequently partially deactivated, e.g. covered by a further layer.

Figure 10:
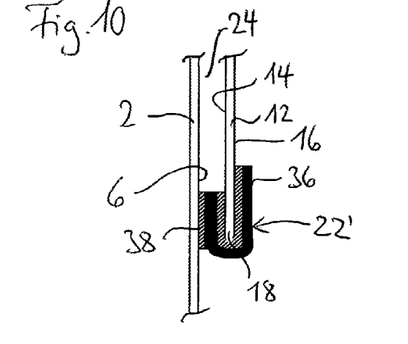

FIG. 10 shows a third preferred embodiment of the joining means 22'. The joining means 22' is disposed between the upper side 6 of the base cover material 2 and the inner side 14 of the absorbent material section 12 such that these are directly connected, and extends further past the peripheral edge 18 of the absorbent material section 12 and is then folded back and fixed to the upper side 16 of the material section 12. A bag 24 is formed between the base cover material 2 and the absorbent material section 12. The joining means 22' has, on both upper sides of the polymeric layer 36, an adhesive coating 38 which has a varying extension. A double-sided adhesive tape may be used for a joining means of this type, the overall upper side of which is provided with an adhesive coating and the opposite upper side of which is only partially provided with an adhesive coating. Advantageously, at most half, and moreover advantageously at most only one quarter of the width of the adhesive tape is adhesive. The corresponding other part is thereby non-adhesive, which may be achieved in that no adhesive coating is applied or that the adhesive coating that extends over the overall width of the tape is subsequently partially deactivated, e.g. covered by a further layer.

Figure 11:
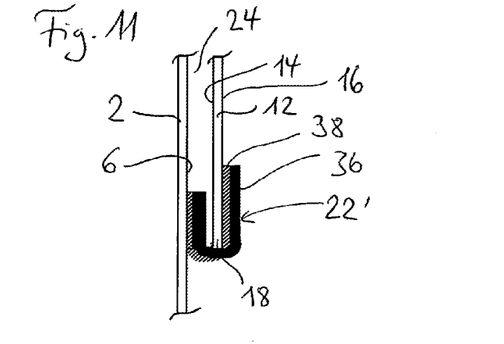

FIG. 11 shows a fourth preferred embodiment of the joining means 22'. The joining means 22' covers the edge area on the outer side 16 of the absorbent material section 12 and extends past the peripheral edge 18 of the absorbent material section 12 and is then folded back towards the bag 24, thereby covering the peripheral edge 18, and fixed to the upper side 6 of the base cover material. A double-sided and moisture-stable adhesive tape with a polymeric layer 36 may be used for a joining means of this type in such a fashion that, as viewed in the longitudinal direction of the adhesive tape, the areas having an adhesive coating 38 and the areas not having an adhesive coating are disposed offset from one another on the upper sides.

Due to the arrangement of the joining means as described in FIGS. 10 and 11, the absorbent material section is additionally sealed from the outside on this peripheral edge by means of the liquid barrier generated by the joining means.

Figure 12:
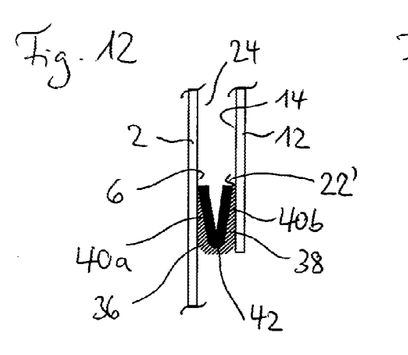
Figure 13:
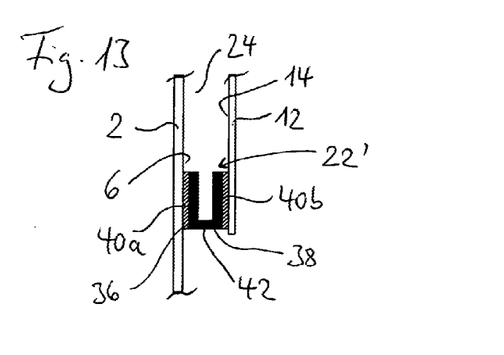

FIGS. 12 and 13 show a fifth preferred embodiment of the joining means 22'. The joining means 22' is configured in the form of a groove. The two legs 40a, 40b of the groove are each fixed, starting from the distal folding edge 42, to the upper side 6 of the base cover material 2 and to the inner side 14 of the absorbent material section 12 such that the groove opens towards the bag 24.

A single-sided and moisture-stable adhesive tape may be used for a joining means of this type. The adhesive coating 38 of the upper side of the polymeric layer 36 may thereby advantageously be discontinuous in the area of the provided folding edge 42 such that no adhesive coating is applied in this area or also that the adhesive coating which is provided on the overall surface per se is deactivated in this area e.g. covered by a further layer.

Figure 14:
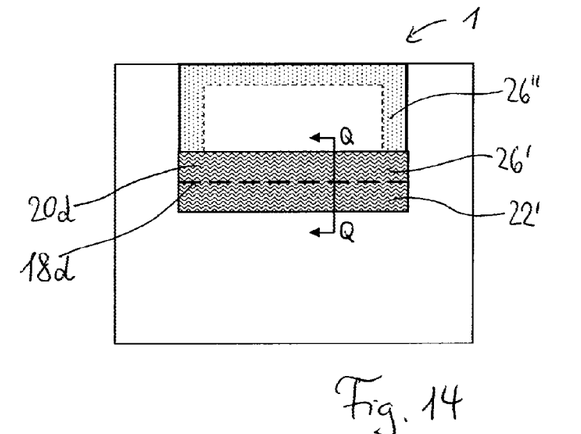
FIG. 14 shows a schematic top view of a surgical cover with a joining means in a further preferred embodiment.
Figure 15:
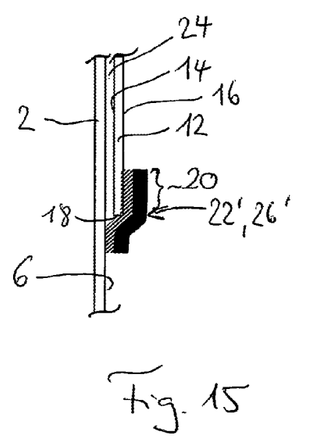
FIG. 15 shows a schematic view of the joining means, arranged in the surgical cover of FIG. 14 along the line Q-Q.

FIGS. 14 and 15 show a sixth preferred embodiment of the joining means 22'.

FIG. 14 schematically shows a top view of a preferred embodiment of a surgical cover 1 as described in connection with FIG. 1, in which at least the lower edge area 20d of the absorbent material section 12, which borders the lower peripheral edge 18d, has a liquid barrier 26' which is provided by the joining means 22' illustrated in more detail in FIG. 15 (side view along the line Q-Q). The other edge areas have a further liquid barrier 26".

In a sixth preferred embodiment, the joining means 22' covers both an edge area 20 on the outer side 16 of the absorbent material section 12 and also a directly bordering part of the upper side 6 of the base cover material 2.

A single-sided and moisture-stable adhesive tape may be used for a joining means of this type.

Figure 16:
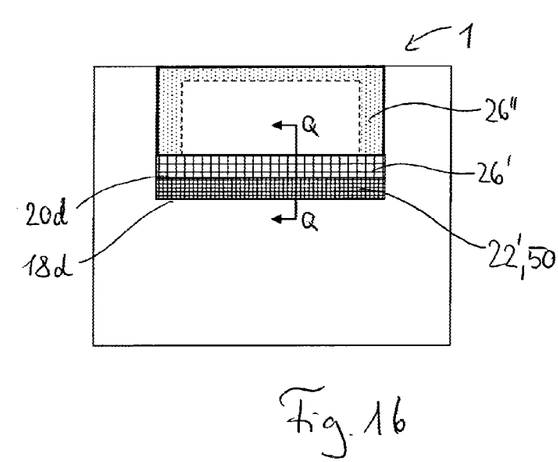
FIG. 16 shows a schematic top view of a surgical cover with a joining means in the form of a welding pattern.
Figure 17:
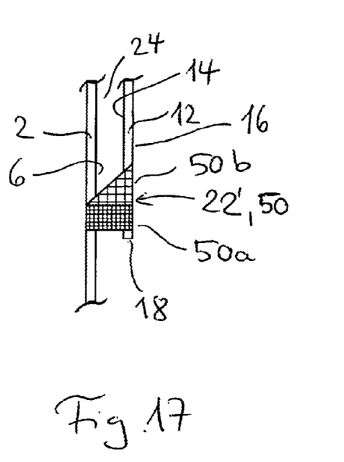
FIG. 17 shows a schematic view of the joining means, arranged in the surgical cover of FIG. 16, along the line Q-Q.

FIGS. 16 and 17 show a seventh preferred embodiment of the joining means 22'. FIG. 16 schematically shows a top view of a surgical cover 1 as described in FIG. 1 with the preferred design that at least the lower edge area 20d of the absorbent material section 12 bordering the lower peripheral edge 18d has a liquid barrier 26' which is provided by the joining means 22' shown in detail in FIG. 17 (side view along the line Q-Q). The other edge areas have a further liquid barrier 26".

The joining means 22' is designed in the form of welding points. The welding points may thereby be ultrasonic welding points, thermal welding points (thermobonding), or calender welding points.

The welding points are thereby disposed in the form of a welding pattern 50. The welding pattern may thereby result from the arrangement of the welding points and their separation from each other, i.e. the welding point density. The welding pattern 50 may also result from the different depths of the welding points. The joining means 22' of this seventh preferred embodiment extends at least past the edge area 20d.

The joining means 22' may also additionally extend past the peripheral edge 18*d* and the bordering part of the base cover material 2 (not shown in the figure).

The welding pattern 50 is designed in such a fashion that its profile decreases, starting from a peripheral edge 18 in the direction towards the bag 24, with respect to the bonding point depth and/or the bonding point density and/or the bonding point strength. A first subregion of the edge area which is disposed proximally to the peripheral edge 18 thereby has a first welding pattern 50*a*. The further subregion facing the bag 24 thereby has a second welding pattern 50*b*. The first welding pattern 50*a* thereby has welding points which form an undetachable fixation between the absorbent material section 12, starting from its upper side 16, and the base cover material 2. The second welding pattern 50*b* is thereby of such a type that only the absorbent material section, in particular only the upper side 16 of the absorbent material section has welding points.

FIG. 18 schematically shows the side view along the line Q-Q from FIG. 7, i.e. the joining means 22', 22" introduced to an outer edge area 20*a* and an inner edge area 20*b* in different embodiments. The inner peripheral edges 18*b* of the absorbent material section 1 are arranged around the recess 30 to be flush with its edges 32. A joining means 22' of a groove-shaped configuration as described in connection with FIG. 12 is introduced to the outer edge area 20*a*. A joining means 22" of a planar configuration as described in connection with FIG. 8 is introduced to the inner edge area 20*b*. Any joining means 22', 22" undetachably fixes the absorbent material section 12 in the respective edge areas 20*a*, 20*b* to the upper side 6 of the base cover material 2, thereby forming the bag 24. The liquid barriers 26', 26" formed by these joining means 22', 22" are different from each other.

The first liquid barrier 26' provided by the groove-shaped joining means 22' on the outer edge area 20*a* represents a stronger liquid barrier than the further liquid barrier 26" provided by the planar joining means 22' on the inner edge area 20*b*.

Figure 19:
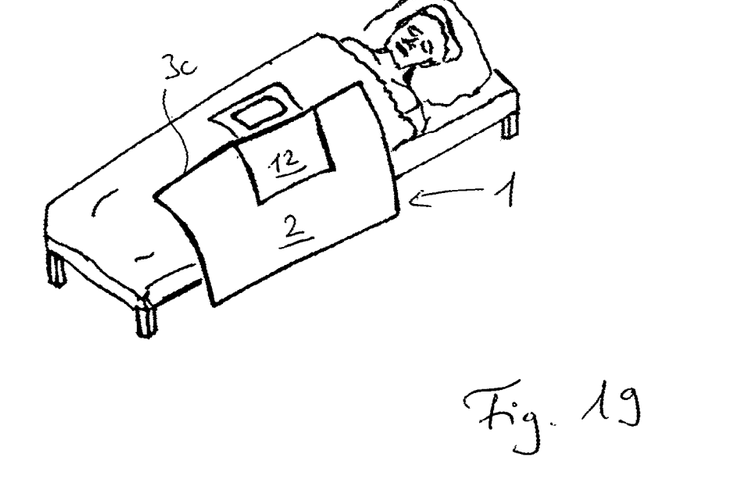
FIG. 19 shows a schematic view of the use of the surgical cover according to FIG. 1.
Figure 20:
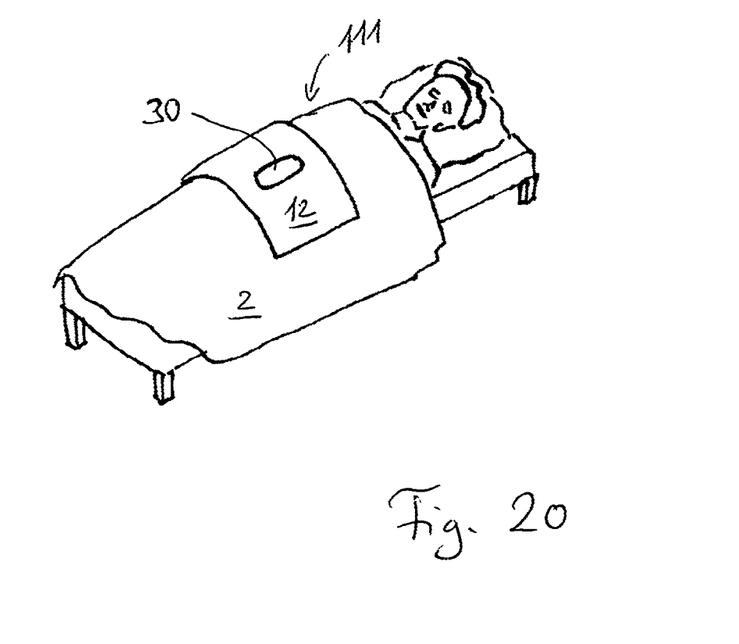
FIG. 20 shows a schematic view of the use of the surgical cover according to FIG. 3.

FIGS. 19 and 20 schematically show possible arrangements of the inventive surgical covers during use.

FIG. 19 shows a surgical cover in accordance with the embodiment according to FIG. 1. The absorbent material section 12 is thereby arranged to be substantially flush with the upper end 3*c* of the surgical cover.

FIG. 19 shows a surgical cover in accordance with the embodiment according to FIG. 3. The absorbent material section 12 is thereby arranged to be substantially flush with the edges of the recess 30 of the surgical cover 111.

Advantageous embodiments of inventive surgical covers:

The surgical cover 1 illustrated in FIG. 5 clearly shows a liquid impermeable base cover material 2 with a lower side 4 facing the patient during use, and an upper side 6, wherein this upper side 6 itself has an absorbent layer.

The base cover material consists of a non-woven foil composite, wherein the non-woven layer facing the upper side 6 consists of a hydrophilized spunbonded non-woven material, in particular, of a hydrophilized PP spunbonded non-woven material. The surface density of the spunbonded non-woven layer is 25 to 35 g/m$^2$. The absorptive capacity AK of this spunbonded non-woven material according to the above-described method is 120 to 180 g/m$^2$. The upper side 6 has a first absorbent area 8 and a second absorbent area 10. This second absorbent area 10 itself is covered by a rectangular material section 12 having an inner side and an outer side which absorbs liquids and is permeable to liquids. This absorbent material section 12 is formed from a hydrophilized SMS non-woven material, in particular, of a hydrophilized PP-SMS non-woven material with a surface density of 50 to 60 g/m$^2$. The absorptive capacity of this SMS non-woven material according to the above-described method is 220 to 330 g/m$^2$.

The absorbent material section 12 with peripheral edges 18 and edge areas 20 bordering the peripheral edges is undetachably fixed in its edge areas across the entire circumference to the upper side 6 of the base cover material. The absorbent material section 12 is substantially not connected to the base cover material outside of these edge areas 20. For this reason, a bag is formed between the absorbent material section 12 and the liquid impermeable base cover material 2. The surgical cover extends in the longitudinal direction LR between an upper end 3*c* and a lower end 3*d*, wherein the absorbent material section is disposed closer to the upper end 3*c* of the surgical cover than to the lower end 3*d* of the surgical cover. In this arrangement, the material section 12 also correspondingly comprises an upper peripheral edge 18*c*, a lower peripheral edge 18*d* and bordering lateral peripheral edges 18*e*, 18*f* and corresponding edge areas 20*c*, 20*d*, 20*e*, 20*f* which border these peripheral edges 18*c*, 18*d*, 18*e*, 18*f*.

The upper peripheral edge 18*c* of the material section is substantially disposed flush with the upper end 3*c* of the surgical cover.

The edge areas 20*c*, 20*d*, 20*e*, 20*f* have a liquid barrier 26', 26", at least in sections, wherein the liquid barrier 26', 26" is formed by a joining means which undetachably fixes the material section to the upper side of the base cover material.

Different joining means 22', 22" are used for the lower edge area 20*d* and for the further edge areas 20*c*, 20*e*, 20*f* such that the lower edge area has a first liquid barrier 26' and the further edge areas have a further liquid barrier 26".

The joining means 22', 22" are advantageously used in the following combinations:

In a first preferred variant of the surgical cover, the joining means 22' is configured in a groove shape in the lower edge area 20*d* in correspondence with the fifth embodiment of the joining means as described in connection with FIGS. 12 and 13.

A single-sided and moisture-stable adhesive tape (such as e.g. MED 248 distributed by the company Köster, Altendorf, Germany) is thereby used as groove-shaped joining means.

Towards this end, the single-sided adhesive tape is folded in its longitudinal direction, thereby forming a folding edge 42 and two legs 40*a*, 40*b*. The folding edge 42 may thereby be disposed at the center. The folding edge may also be disposed eccentrically with respect to the width of the adhesive tape. The adhesive tape is applied in such a fashion that the folding edge 42 terminates substantially flush with the lower peripheral edge 18*d* of the absorbent material section 12 and the two legs 40*a*, 40*b* are fixed with their respective adhesive upper side to the inner side 14 of the absorbent material section and to the upper side 6 of the base cover material. The groove opens towards the bag 24, thereby forming a first liquid barrier 26' in the lower edge area 20*d*.

In a second preferred variant of the surgical cover, the joining means 22' is designed and fixed in the lower edge area 20*d* in correspondence with the fourth preferred embodiment of the joining means as described in connection with FIG. 11.

In a third preferred variant of the surgical cover, the joining means 22' in the lower edge area 20*d* is designed and fixed in correspondence with the sixth preferred embodiment of the joining means as described in connection with FIG. 15.

A single-sided and moisture-stable adhesive tape can be used as joining means that covers both the outer side of the absorbent material section and also the part of the upper side 6 of the base cover material 2 directly bordering the edge area, wherein the adhesive upper side of the adhesive tape faces the outer side 16 and upper side 6.

In a fourth preferred variant of the surgical cover, the joining means 22' is designed and fixed in the lower edge area 20d in correspondence with the seventh preferred embodiment of the joining means as described in connection with FIGS. 16 and 17.

In a fifth preferred variant of the surgical cover, the joining means 22' is designed and fixed in the lower edge area 20d in correspondence with the second embodiment of the joining means explained in more detail above, as described in connection with FIG. 9.

In a sixth preferred variant of the surgical cover, the joining means 22' is designed and fixed in the lower edge area 20d in correspondence with the third embodiment of the joining means explained in more detail above, as described in connection with FIG. 10.

For all above-mentioned variants of the surgical cover, joining means 22', 22" are preferably used for the other edge areas 20c, 20e, 20f, which are flatly disposed between the upper side of the base cover material 2 and the inner side of the absorbent material section in correspondence with the first preferred embodiment according to FIG. 8 or also advantageously in correspondence with the second preferred embodiment according to FIG. 9.

These edge areas 20c, 20e, 20f are fixed by means of a hot melt adhesive. These edge areas 20c, 20e, 20f may also be fixed by means of a double-sided moisture-stable adhesive tape.

The surgical cover 1 illustrated in FIG. 6 differs from the above-described surgical cover illustrated in FIG. 5 and from its variants in that the joining means 22' used in the lower edge area 20d are also used in the edge areas 20e, 20f which each laterally border the lower edge area 20d for undetachably fixing the absorbent material section to the upper side of the base cover material.

Only the upper edge area 20c is correspondingly advantageously fixed with a flat joining means between the upper side 6 of the base cover material 2 and the inner side 14 of the absorbent material section in correspondence with the first embodiment according to FIG. 8, i.e. in the form of a hot melt adhesive or also a double-sided adhesive tape, thereby forming the further liquid barrier 26".

The hot melt adhesive may e.g. be Nolax M11.123 distributed by the company Collano, Sempach, Switzerland.

It is also feasible for all edge areas 20c, 20d, 20e, 20f to have the same liquid barrier 26'. This liquid barrier 26' is formed by a joining means 22' which undetachably fixes the material section 12 along all edge areas 20c, 20d, 20e, 20f to the upper side of the base cover material. All described embodiments of the joining means can be used for this purpose.

Although it is not illustrated in more detail, surgical covers 11, 111 having a recess 30 (as schematically illustrated in FIGS. 3 and 4) may also comprise all features of the above-described surgical cover with respect to material properties/composition of the base cover material and of the absorbent material section.

The joining means 22', 22" used at the respective outer and inner edge areas 20a, 20b differ from each other such that a first 26' and a further liquid barrier 26" are correspondingly formed at least in sections of the outer and inner edge area.

The outer and inner edge areas themselves can again be fixed in the upper, lower and those edge areas that laterally adjoin the lower edge area with different joining means, thereby forming further liquid barriers.

I claim:

1. A disposable surgical cover for a patient, the disposable surgical cover comprising:
    a liquid-impermeable base cover, said liquid-impermeable base cover having a lower side facing the patient during use and an upper side, said liquid-impermeable base cover extending in a longitudinal direction between an upper end and a lower end thereof;
    an absorbent layer disposed at said upper side of said liquid-impermeable base cover, said absorbent layer defining a first absorbent area and at least one second absorbent area;
    a material section, said material section disposed directly above and covering said second absorbent area without interposition of any additional material, said material section having peripheral edges and edge areas adjacent to said peripheral edges, wherein said material section is liquid-absorbent and liquid-permeable, said material section having an inner side and an outer side; and
    joining means, said joining means configured to permanently fix said material section to said absorbent layer across an entire circumference in said edge areas, said material section being substantially free of connection to said liquid-impermeable base cover outside of said edge areas, thereby forming an empty bag, said empty bag having an upper inner surface formed by said inner side of said material section and a lower inner surface formed by said second absorbent area, wherein said joining means generates a liquid barrier at at least one of said edge areas of said material section and a surface of said absorbent layer which is not covered by said material section forms said first absorbent area.

2. The disposable surgical cover of claim 1, wherein the disposable surgical cover has at least one recess at said second absorbent area, said recess having edges.

3. The disposable surgical cover of claim 2, wherein said second absorbent area directly surrounds and borders said recess, the material section having inner peripheral edges and inner edge areas, which are associated with said edges of said recess, as well as outer peripheral edges and outer edge areas.

4. The disposable surgical cover of claim 3, wherein said inner peripheral edges of said material section are disposed to be substantially flush with said edges of said recess.

5. The disposable surgical cover of claim 1, wherein said material section is disposed closer to said upper end of said liquid-impermeable base cover than to said lower end of said liquid-impermeable base cover.

6. The disposable surgical cover of claim 5, wherein an upper peripheral edge of said material section is substantially flush with said upper end of said liquid-impermeable base cover.

7. The disposable surgical cover of claim 1, wherein said joining means are selected from the group consisting of hot melt adhesive, single-sided adhesive tape, double sided adhesive tape, welding points, ultrasonic welding points, thermal welding points and calender welding points.

8. The disposable surgical cover of claim 7, wherein welding points are arranged in a welding pattern covering a bordering edge area, a profile of said welding pattern thereby decreasing towards said bag, with respect to bonding point depth, bonding point density or bonding point strength.

9. The disposable surgical cover of claim 1, wherein a lower edge area of said material section has said liquid barrier.

10. The disposable surgical cover of claim 9, wherein edge areas of said material section that adjoin each side of a lower edge area of said material section have said liquid barrier.

11. The disposable surgical cover of said 1, wherein only outer edge areas of said material section have said liquid barrier.

12. The disposable surgical cover of claim 1, wherein said joining means constitute a first and at least one further liquid barrier.

13. The disposable surgical cover of claim 1, wherein said liquid barrier is disposed on said inner side or said outer side of said material section.

14. The disposable surgical cover of claim 1, wherein said joining means is flatly disposed between said upper side of said liquid-impermeable base cover and said inner side of said material section.

15. The disposable surgical cover of claim 1, wherein said joining means is connected between said upper side of said liquid-impermeable base cover and said inner side of said material section, extends past said peripheral edge of said absorbent material section, is folded back and fixed to said upper side of said material section.

16. The disposable surgical cover of claim 1, wherein said joining means is disposed on said upper side of said liquid-impermeable base cover, extends past said peripheral edge of said material section and is folded back and fixed to said upper side of said material section.

17. The disposable surgical cover of claim 1, wherein said joining means is groove-shaped and is fixed between said upper side of said liquid-impermeable base cover and said inner side of said material section, wherein said joining means opens towards said bag.

18. The disposable surgical cover of claim 1, wherein said joining means covers both an edge area on said outer side of said material section and a directly bordering part of said upper side of said liquid-impermeable base cover.

19. The disposable surgical cover of claim 1, wherein said liquid barrier extends past a width of a fixed edge area in a direction towards said bag.

20. The disposable surgical cover of claim 1, wherein fixed edge areas cover a surface of 2 to 45% of an overall surface of said material section.

21. The disposable surgical cover of claim 1, wherein said edge areas have a width B of 0.5 to 10 cm.

22. The disposable surgical cover of claim 1, wherein said material section has an absorptive capacity which is larger than an absorptive capacity of a material forming said first absorbent area.

23. The disposable surgical cover of claim 1, wherein said material section has a relative absorptive capacity of at least 150 g/m$^2$.

24. The disposable surgical cover of claim 1, wherein a material forming said first absorbent area has an absorptive capacity of 50 to 250 g/m$^2$.

25. The disposable surgical cover of claim 1, wherein said second absorbent area has an area of 2 to 65% relative to an overall surface area of said liquid-impermeable base cover.

26. The disposable surgical cover of claim 1, wherein said material section is formed by a non-woven material having one or more layers.

27. The disposable surgical cover of claim 1, wherein said material section consists essentially of a hydrophilized non-woven material with one or several spunbonded or meltblown layers.

28. The disposable surgical cover of claim 1, wherein said material section has a surface density of 25 to 100 g/m$^2$.

29. The disposable surgical cover of claim 1, wherein said liquid-impermeable base cover is formed from a single-layer or multi-layer non-woven material, a laminate of one or more spunbonded non-woven or meltblown non-woven material layers or a non-woven foil composite.

30. The disposable surgical cover of claim 1, wherein said liquid-impermeable base cover consists essentially of a two-layer non-woven foil composite with a non-woven material of a hydrophilized spunbonded non-woven material, wherein said lower side is defined by foil material.

* * * * *